(12) United States Patent
Alferness et al.

(10) Patent No.: US 8,172,898 B2
(45) Date of Patent: May 8, 2012

(54) DEVICE AND METHOD FOR MODIFYING THE SHAPE OF A BODY ORGAN

(75) Inventors: Clifton A. Alferness, Port Orchard, OR (US); John M. Adams, Kirkland, WA (US); Mark L. Mathis, Fremont, CA (US); David G. Reuter, Bothell, WA (US); Cruz Beeson, Chico, CA (US); Leonard Kowalsky, Bothell, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 0 days.

(21) Appl. No.: 12/719,758

(22) Filed: Mar. 8, 2010

(65) Prior Publication Data
US 2010/0168847 A1    Jul. 1, 2010

Related U.S. Application Data

(63) Continuation of application No. 11/467,105, filed on Aug. 24, 2006, now Pat. No. 7,674,287, which is a continuation of application No. 10/429,171, filed on May 2, 2003, now Pat. No. 7,179,282.

(51) Int. Cl.
*A61F 2/24* (2006.01)
*A61F 2/06* (2006.01)

(52) U.S. Cl. ....... 623/2.36; 623/1.11; 623/2.1; 623/2.37

(58) Field of Classification Search ................. 623/1.11, 623/1.15, 2.1, 2.36, 2.37
See application file for complete search history.

(56) References Cited

U.S. PATENT DOCUMENTS

| | | | |
|---|---|---|---|
| 3,620,212 A | 11/1971 | Fannon, Jr. et al. |
| 3,786,806 A | 1/1974 | Johnson et al. |
| 3,890,977 A | 6/1975 | Wilson |
| 3,974,526 A | 8/1976 | Dardik et al. |
| 3,995,623 A | 12/1976 | Black et al. |
| 4,055,861 A | 11/1977 | Carpentier et al. |
| 4,164,046 A | 8/1979 | Cooley |
| 4,485,816 A | 12/1984 | Krumme |

(Continued)

FOREIGN PATENT DOCUMENTS
EP    0893133    1/1999
(Continued)

OTHER PUBLICATIONS

EL-Maasarany et al.; The coronary sinus conduit function: Anatomical study (relationship to adjacent structures); http://europace.oxfordjournals.org/cge/content/full/7/5/475. (accessed Sep. 9, 2008).

(Continued)

*Primary Examiner* — David Isabella
*Assistant Examiner* — Yashita Sharma
(74) *Attorney, Agent, or Firm* — Shay Glenn LLP

(57) ABSTRACT

An intravascular support device includes a support or reshaper wire, a proximal anchor and a distal anchor. The support wire engages a vessel wall to change the shape of tissue adjacent the vessel in which the intravascular support is placed. The anchors and support wire are designed such that the vessel in which the support is placed remains open and can be accessed by other devices if necessary. The device provides a minimal metal surface area to blood flowing within the vessel to limit the creation of thrombosis. The anchors can be locked in place to secure the support within the vessel.

8 Claims, 15 Drawing Sheets

U.S. PATENT DOCUMENTS

| | | | |
|---|---|---|---|
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,099,838 A | 3/1992 | Bardy | |
| 5,104,404 A | 4/1992 | Wolff | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,433,727 A | 7/1995 | Sideris | |
| 5,441,515 A | 8/1995 | Khosravi et al. | |
| 5,449,373 A | 9/1995 | Pinchasik et al. | |
| 5,454,365 A | 10/1995 | Bonutti | |
| 5,458,615 A | 10/1995 | Klemm et al. | |
| 5,474,557 A | 12/1995 | Mai | |
| 5,507,295 A | 4/1996 | Skidmore | |
| 5,507,802 A | 4/1996 | Imran | |
| 5,514,161 A | 5/1996 | Limousin | |
| 5,554,177 A | 9/1996 | Kieval et al. | |
| 5,562,698 A | 10/1996 | Parker | |
| 5,575,818 A | 11/1996 | Pinchuk | |
| 5,584,867 A | 12/1996 | Limousin et al. | |
| 5,601,600 A | 2/1997 | Ton | |
| 5,617,854 A | 4/1997 | Munsif | |
| 5,662,703 A | 9/1997 | Yurek et al. | |
| 5,676,671 A | 10/1997 | Inoue | |
| 5,733,325 A | 3/1998 | Robinson et al. | |
| 5,741,297 A | 4/1998 | Simon | |
| 5,752,969 A | 5/1998 | Cunci et al. | |
| 5,800,519 A | 9/1998 | Sandock | |
| 5,824,071 A | 10/1998 | Nelson et al. | |
| 5,836,882 A | 11/1998 | Frazin | |
| 5,871,501 A | 2/1999 | Leschinsky et al. | |
| 5,891,193 A | 4/1999 | Robinson et al. | |
| 5,895,391 A | 4/1999 | Farnholtz | |
| 5,899,882 A | 5/1999 | Waksman et al. | |
| 5,908,404 A | 6/1999 | Elliot | |
| 5,928,258 A | 7/1999 | Khan et al. | |
| 5,935,161 A | 8/1999 | Robinson et al. | |
| 5,954,761 A | 9/1999 | Machek et al. | |
| 5,961,545 A | 10/1999 | Lentz et al. | |
| 5,978,705 A | 11/1999 | KenKnight et al. | |
| 5,984,944 A | 11/1999 | Forber | |
| 6,007,519 A | 12/1999 | Rosselli | |
| 6,015,402 A | 1/2000 | Sahota | |
| 6,022,371 A | 2/2000 | Killion | |
| 6,027,517 A | 2/2000 | Crocker et al. | |
| 6,045,497 A | 4/2000 | Schweich, Jr. et al. | |
| 6,053,900 A | 4/2000 | Brown et al. | |
| 6,056,775 A | 5/2000 | Borghi et al. | |
| 6,077,295 A | 6/2000 | Limon et al. | |
| 6,077,297 A | 6/2000 | Robinson et al. | |
| 6,080,182 A | 6/2000 | Shaw et al. | |
| 6,086,611 A | 7/2000 | Duffy et al. | |
| 6,096,064 A | 8/2000 | Routh | |
| 6,099,549 A | 8/2000 | Bosma et al. | |
| 6,099,552 A | 8/2000 | Adams | |
| 6,129,755 A | 10/2000 | Mathis et al. | |
| 6,171,320 B1 | 1/2001 | Monassevitch | |
| 6,183,512 B1 | 2/2001 | Howanec et al. | |
| 6,190,406 B1 | 2/2001 | Duerig et al. | |
| 6,200,336 B1 | 3/2001 | Pavcnik et al. | |
| 6,210,432 B1 | 4/2001 | Solem et al. | |
| 6,228,098 B1 | 5/2001 | Kayan et al. | |
| 6,241,757 B1 | 6/2001 | An et al. | |
| 6,254,628 B1 | 7/2001 | Wallace et al. | |
| 6,267,783 B1 | 7/2001 | Letendre et al. | |
| 6,275,730 B1 | 8/2001 | KenKnight et al. | |
| 6,306,141 B1 | 10/2001 | Jervis | |
| 6,312,446 B1 | 11/2001 | Huebsch et al. | |
| 6,334,864 B1 | 1/2002 | Amplatz et al. | |
| 6,342,067 B1 | 1/2002 | Mathis et al. | |
| 6,345,198 B1 | 2/2002 | Mouchawar et al. | |
| 6,352,553 B1 | 3/2002 | van der Burg et al. | |
| 6,352,561 B1 | 3/2002 | Leopold et al. | |
| 6,358,195 B1 | 3/2002 | Green et al. | |
| 6,395,017 B1 | 5/2002 | Dwyer et al. | |
| 6,402,781 B1 | 6/2002 | Langberg et al. | |
| 6,419,696 B1 | 7/2002 | Ortiz et al. | |
| 6,442,427 B1 | 8/2002 | Boute et al. | |
| 6,464,720 B2 | 10/2002 | Boatman et al. | |
| 6,478,776 B1 | 11/2002 | Rosenman et al. | |
| 6,503,271 B2 | 1/2003 | Duerig et al. | |
| 6,537,314 B2 | 3/2003 | Langberg et al. | |
| 6,556,873 B1 | 4/2003 | Smits | |
| 6,562,066 B1 * | 5/2003 | Martin | 623/1.15 |
| 6,562,067 B2 | 5/2003 | Mathis | |
| 6,569,198 B1 | 5/2003 | Wilson et al. | |
| 6,589,208 B2 | 7/2003 | Ewers et al. | |
| 6,599,314 B2 | 7/2003 | Mathis et al. | |
| 6,602,288 B1 | 8/2003 | Cosgrove et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,629,534 B1 | 10/2003 | St. Goar et al. | |
| 6,629,994 B2 | 10/2003 | Gomez et al. | |
| 6,643,546 B2 | 11/2003 | Mathis et al. | |
| 6,648,881 B2 | 11/2003 | KenKnight et al. | |
| 6,652,538 B2 | 11/2003 | Kayan et al. | |
| 6,656,221 B2 | 12/2003 | Taylor et al. | |
| 6,676,702 B2 | 1/2004 | Mathis | |
| 6,689,164 B1 | 2/2004 | Seguin | |
| 6,709,425 B2 | 3/2004 | Gambale et al. | |
| 6,716,158 B2 | 4/2004 | Raman et al. | |
| 6,718,985 B2 | 4/2004 | Hlavka et al. | |
| 6,721,598 B1 | 4/2004 | Helland et al. | |
| 6,723,038 B1 | 4/2004 | Schroeder et al. | |
| 6,733,521 B2 | 5/2004 | Chobotov et al. | |
| 6,743,219 B1 | 6/2004 | Dwyer et al. | |
| 6,764,510 B2 | 7/2004 | Vidlund et al. | |
| 6,773,446 B1 | 8/2004 | Dwyer et al. | |
| 6,776,784 B2 | 8/2004 | Ginn | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,798,231 B2 | 9/2004 | Iwasaki et al. | |
| 6,800,090 B2 | 10/2004 | Alferness et al. | |
| 6,805,128 B1 | 10/2004 | Pless et al. | |
| 6,810,882 B2 | 11/2004 | Langberg et al. | |
| 6,821,297 B2 | 11/2004 | Snyders | |
| 6,824,562 B2 | 11/2004 | Mathis et al. | |
| 6,827,690 B2 | 12/2004 | Bardy | |
| 6,881,220 B2 | 4/2005 | Edwin et al. | |
| 6,899,734 B2 | 5/2005 | Castro et al. | |
| 6,908,478 B2 | 6/2005 | Alferness et al. | |
| 6,908,482 B2 | 6/2005 | McCarthy et al. | |
| 6,935,404 B2 | 8/2005 | Duerig et al. | |
| 6,949,122 B2 | 9/2005 | Adams et al. | |
| 6,955,689 B2 | 10/2005 | Ryan et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,976,995 B2 | 12/2005 | Mathis et al. | |
| 7,004,958 B2 | 2/2006 | Adams et al. | |
| 7,152,605 B2 | 12/2006 | Khairkhahan et al. | |
| 7,175,653 B2 | 2/2007 | Gaber | |
| 7,179,282 B2 | 2/2007 | Alferness et al. | |
| 7,309,354 B2 | 12/2007 | Mathis et al. | |
| 7,311,729 B2 | 12/2007 | Mathis et al. | |
| 7,316,708 B2 | 1/2008 | Gordon et al. | |
| 7,364,588 B2 | 4/2008 | Mathis et al. | |
| 7,452,375 B2 | 11/2008 | Mathis et al. | |
| 7,591,826 B2 | 9/2009 | Alferness et al. | |
| 2001/0018611 A1 | 8/2001 | Solem et al. | |
| 2001/0041899 A1 | 11/2001 | Foster | |
| 2001/0044568 A1 | 11/2001 | Langberg et al. | |
| 2001/0049558 A1 | 12/2001 | Liddicoat et al. | |
| 2002/0016628 A1 | 2/2002 | Langberg et al. | |
| 2002/0042621 A1 | 4/2002 | Liddicoat et al. | |
| 2002/0042651 A1 | 4/2002 | Liddicoat et al. | |
| 2002/0049468 A1 | 4/2002 | Streeter et al. | |
| 2002/0055774 A1 | 5/2002 | Liddicoat | |
| 2002/0065554 A1 | 5/2002 | Streeter | |
| 2002/0095167 A1 | 7/2002 | Liddicoat et al. | |
| 2002/0138044 A1 | 9/2002 | Streeter et al. | |
| 2002/0151961 A1 | 10/2002 | Lashinski et al. | |

| | | |
|---|---|---|
| 2002/0156526 A1 | 10/2002 | Hlavka et al. |
| 2002/0161377 A1 | 10/2002 | Rabkin et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149182 A1 | 7/2005 | Alferness et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0191121 A1 | 8/2006 | Gordon |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |
| 2007/0135912 A1 | 6/2007 | Mathis |
| 2007/0239270 A1 | 10/2007 | Mathis et al. |

| | | |
|---|---|---|
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2008/0097594 A1 | 4/2008 | Mathis et al. |
| 2008/0109059 A1 | 5/2008 | Gordon et al. |
| 2008/0140191 A1 | 6/2008 | Mathis et al. |
| 2008/0319542 A1 | 12/2008 | Nieminen et al. |
| 2010/0031793 A1 | 2/2010 | Hayner et al. |
| 2010/0100175 A1 | 4/2010 | Reuter et al. |
| 2010/0280602 A1 | 11/2010 | Mathis |
| 2011/0106117 A1 | 5/2011 | Mathis et al. |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO 98/56435 A1 | 12/1998 |
| WO | WO 00/44313 A1 | 8/2000 |
| WO | WO 00/60995 A2 | 10/2000 |
| WO | WO 00/74603 A1 | 12/2000 |
| WO | WO 01/00111 A1 | 1/2001 |
| WO | WO 01/19292 A1 | 3/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03/049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. 1997; 96(6): 1893-1898.

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

Nieminen et al.; U.S. Appl. No. 12/907,907 entitled "Tissue Shaping Device," filed Oct. 19, 2010.

Gordon et al.; U.S. Appl. No. 12/952,057 entitled "Percutaneous Mitral Valve Annuloplasty Delivery System," filed Nov. 22, 2010.

Pelton et al. Medical uses of nitinol; Material Science Forum; vols. 327-328; pp. 63-70; 2000.

Hayner et al.; U.S. Appl. No. 13/220,444 entitled "Catheter cutting tool," filed Aug. 29, 2011.

* cited by examiner

DEVICE AND METHOD FOR MODIFYING THE SHAPE OF A BODY ORGAN

CROSS-REFERENCE TO RELATED APPLICATIONS

The present application is a continuation of U.S. application Ser. No. 11/467,105, filed Aug. 24, 2006, now U.S. Pat. No. 7,674,287; which is a continuation of U.S. application Ser. No. 10/429,171 filed May 2, 2003, now U.S. Pat. No. 7,179,282, the disclosures of which are incorporated by reference in their entirety as if fully set forth herein.

FIELD OF THE INVENTION

The present invention relates to medical devices in general, and in particular to devices for supporting internal body organs.

BACKGROUND OF THE INVENTION

The mitral valve is a portion of the heart that is located between the chambers of the left atrium and the left ventricle. When the left ventricle contracts to pump blood throughout the body, the mitral valve closes to prevent the blood being pumped back into the left atrium. In some patients, whether due to genetic malformation, disease or injury, the mitral valve fails to close properly causing a condition known as regurgitation, whereby blood is pumped into the atrium upon each contraction of the heart muscle. Regurgitation is a serious, often rapidly deteriorating, condition that reduces circulatory efficiency and must be corrected.

Two of the more common techniques for restoring the function of a damaged mitral valve are to surgically replace the valve with a mechanical valve or to suture a flexible ring around the valve to support it. Each of these procedures is highly invasive because access to the heart is obtained through an opening in the patient's chest. Patients with mitral valve regurgitation are often relatively frail thereby increasing the risks associated with such an operation.

One less invasive approach for aiding the closure of the mitral valve involves the placement of a support structure in the cardiac sinus and vessel that passes adjacent the mitral valve. The support structure is designed to push the vessel and surrounding tissue against the valve to aid its closure. This technique has the advantage over other methods of mitral valve repair because it can be performed percutaneously without opening the chest wall. While this technique appears promising, some proposed supports appear to limit the amount of blood that can flow through the coronary sinus and may contribute to the formation of thrombosis in the vessel. Therefore, there is a need for a tissue support structure that does not inhibit the flow of blood in the vessel in which it is placed and reduces the likelihood of thrombosis formation. Furthermore, the device should be flexible and securely anchored such that it moves with the body and can adapt to changes in the shape of the vessel over time.

SUMMARY OF THE INVENTION

The present invention is an intravascular support that is designed to change the shape of a body organ that is adjacent to a vessel in which the support is placed. In one embodiment of the invention, the support is designed to aid the closure of a mitral valve. The support is placed in a coronary sinus and vessel that are located adjacent the mitral valve and urges the vessel wall against the valve to aid its closure.

The intravascular support of the present invention includes a proximal and distal anchor and a support wire or reshaper disposed therebetween. The proximal and distal anchors circumferentially engage a vessel in which the support is placed. A support wire is urged against the vessel by the proximal and distal anchors to support the tissue adjacent the vessel.

In one embodiment of the invention, the proximal and distal supports are made from a wire hoop that presents a low metal coverage area to blood flowing within the vessel. The wire hoops may allow tissue to grow over the anchors to reduce the chance of thrombosis formation. The wire hoops have a figure eight configuration and can expand to maintain contact with the vessel walls if no vessel expands or changes shape.

In another embodiment of the invention, the proximal and distal anchors of the intravascular support are rotationally offset from each other. Locks on the support wire allow a physician to ensure that the anchors have been successfully deployed and prevent the support wire from collapsing within a vessel.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

As indicated above, the present invention is a medical device that supports or changes the shape of tissue that is adjacent a vessel in which the device is placed. The present invention can be used in any location in the body where the tissue needing support is located near a vessel in which the device can be deployed. The present invention is particularly useful in supporting a mitral valve in an area adjacent a coronary sinus and vessel. Therefore, although the embodiments of the invention described are designed to support a mitral valve, those skilled in the art will appreciate that the invention is not limited to use in supporting a mitral valve.

Figure 1:
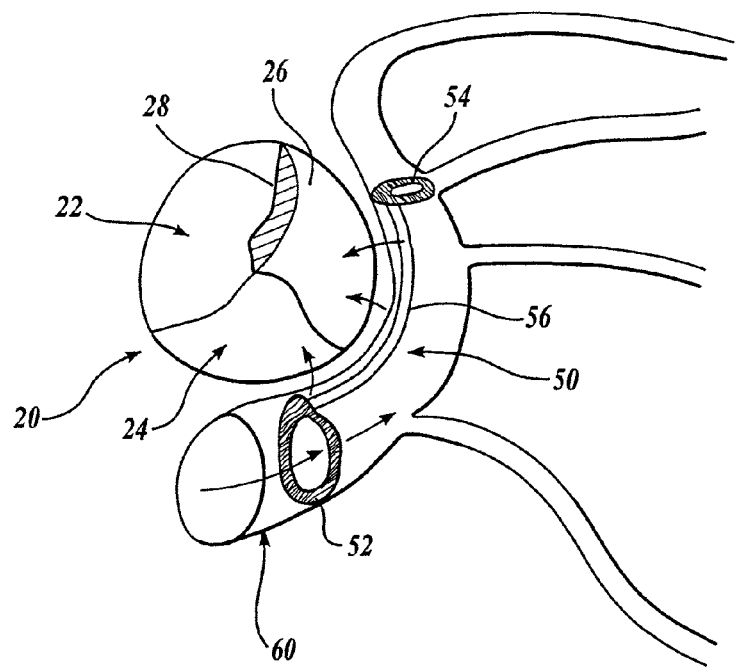
FIG. 1 illustrates an intravascular support for changing the shape of an internal body organ in accordance with one embodiment of the present invention.

FIG. 1 illustrates a mitral valve 20 having a number of flaps 22, 24, and 26 that should overlap and close when the ventricle of the heart contracts. As indicated above, some hearts may have a mitral valve that fails to close properly thereby creating one or more gaps 28 that allow blood to be pumped back into the left atrium each time the heart contracts. To add support to the mitral valve such that the valve completely closes, an intravascular support 50 is placed in a coronary sinus and vessel 60 that passes adjacent one side of the mitral valve 20. The intravascular support 50 has a proximal anchor 52, a distal anchor 54, and a support wire 56 or reshaper extending between the proximal and distal anchors. With the anchors 52 and 54 in place, the support wire 56 exerts a force through the coronary sinus wall on the postero-lateral mitral valve 20 thereby closing the one or more gaps 28 formed between the valve flaps. With the intravascular support 50 in place, the function of the mitral valve is improved.

As will be explained in further detail below, each of the proximal and distal anchors 52, 54 preferably circumferentially engages the wall of the vessel 60 in which it is placed. The support wire 56 is secured to a peripheral edge of the proximal and distal anchors such that the support wire is urged by the anchors against the vessel wall. Therefore, the support wire 56 and anchors 52, 54 present a minimal obstruction to blood flowing within the vessel.

Figure 2:
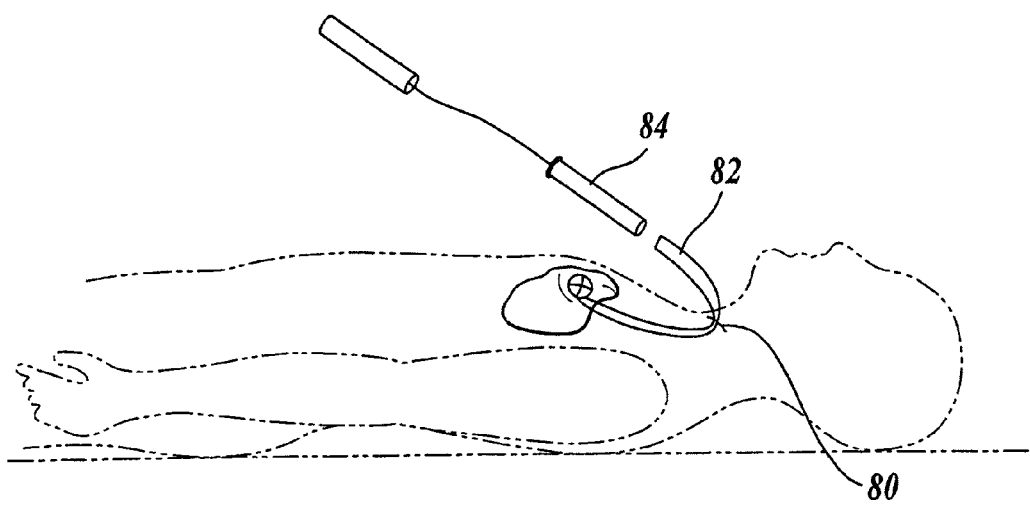
FIG. 2 illustrates one method of deploying an intravascular support in accordance with the present invention.

FIG. 2 shows one possible method of delivering the intravascular support of the present invention to a desired location in a patient's body. An incision 80 is made in the patient's skin to access a blood vessel. A guide catheter 82 is advanced through the patient's vasculature until its distal end is positioned adjacent the desired location of the intravascular support. After positioning the guide catheter 82, a delivery catheter and advancing mechanism 84 are inserted through the guide catheter 82 to deploy the intravascular support at the desired location in the patient's body. Further detail regarding one suitable advancing mechanism 84 is described in commonly assigned U.S. patent application Ser. No. 10/313,914, filed Dec. 5, 2002, the disclosure of which is hereby incorporated by reference.

Figure 3:
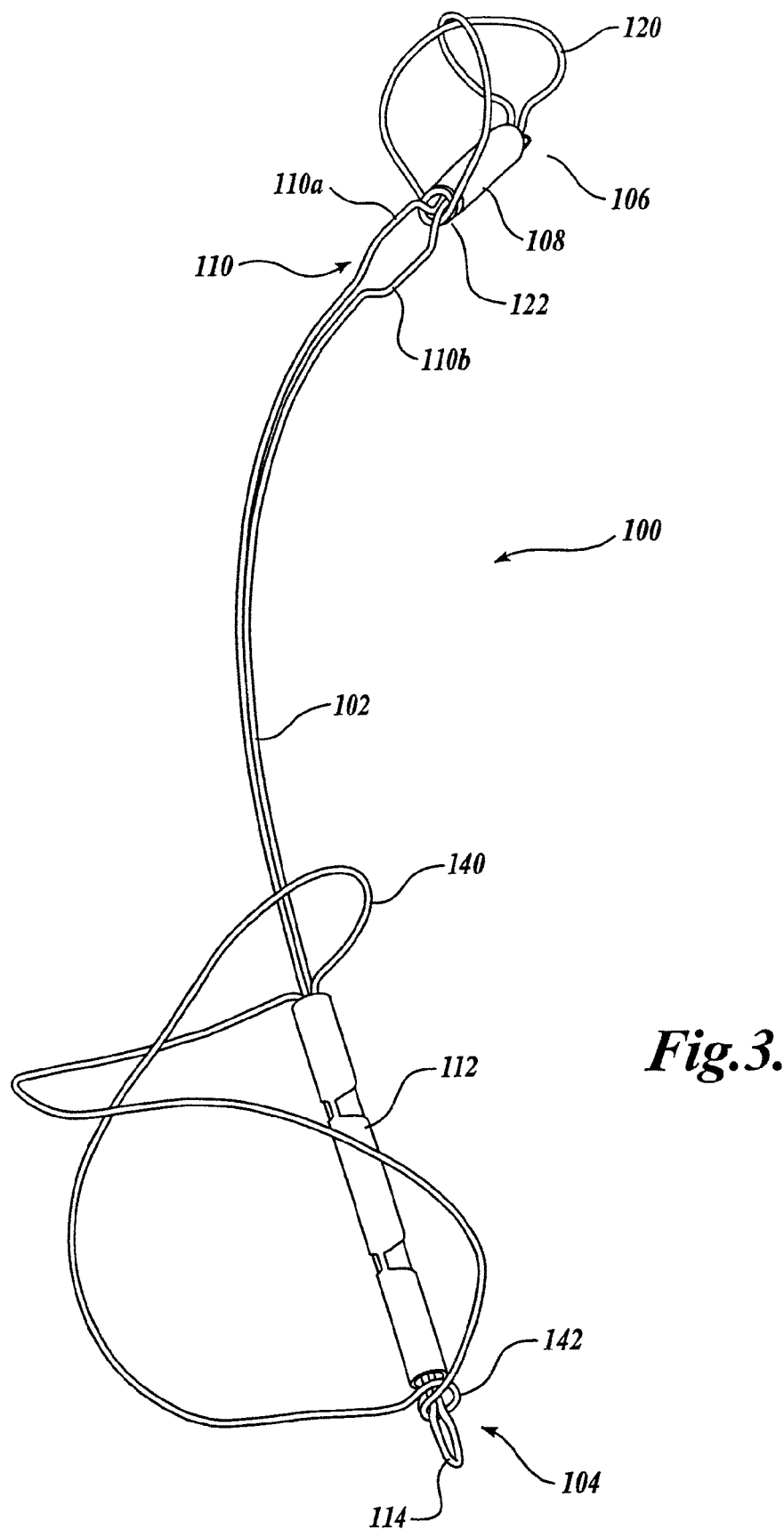
FIG. 3 illustrates one embodiment of the intravascular support in accordance with the present invention.

FIG. 3 illustrates one embodiment of an intravascular support in accordance with the present invention. The intravascular support 100 includes a support wire 102 having a proximal end 104 and a distal end 106. The support wire 102 is made of a biocompatible material such as stainless steel or a shape memory material such as nitinol wire.

In one embodiment of the invention, the support wire 102 comprises a double length of nitinol wire that has both ends positioned within a distal crimp tube 108. To form the support wire 102, the wire extends distally from the crimp tube 108 where it is bent to form a distal stop loop (see 121 in FIG. 4) having a diameter that is larger than the lumens within the distal crimp tube 108. After forming the distal stop loop, the wire returns proximally through the crimp tube 108 towards the proximal end of the support 100. Proximal to the proximal end of the crimp tube 108, is a distal lock 110 that is formed by the support wire bending away from the longitudinal axis of the support 102 and then being bent parallel to the longitudinal axis of the support before being bent again towards the longitudinal axis of the support. Therefore, the bends in the support wire form a half 110a of the distal lock that is used to secure the distal anchor in the manner described below. From the distal lock 110, the wire continues proximally through a proximal crimp tube 112. On exiting the proximal end of the proximal crimp tube 112, the wire is bent to form an arrowhead-shaped proximal lock 114. The wire of the support 102 then returns distally through the proximal crimp tube 112 to a position just proximal to the proximal end of the distal crimp tube 108 wherein the wire is bent to form a second half 110b of the distal lock 110.

Support wire 102 has a length that is selected based on its intended destination within a patient's vessel. For use in supporting a mitral valve, the support wire is preferably between one and six inches long and has a curved bend between its proximal end 104 and distal end 106 with a radius of curvature between 1 and 3 inches and most preferably with a radius of curvature of 1.8 inches. In addition, the wire used to form the support wire 102 is flexible enough to move with each heartbeat (thereby changing the force applied to the mitral valve annulus during the heartbeat) and stiff enough to support the mitral valve. In one embodiment, the wire used to form the support wire 102 is made of nitinol having a modulus of elasticity of $5-20 \times 10^6$ psi and a diameter of between 0.0110" and 0.0150" and most preferably 0.0140". Other shape memory materials may be used for support wire as well.

Figure 4:
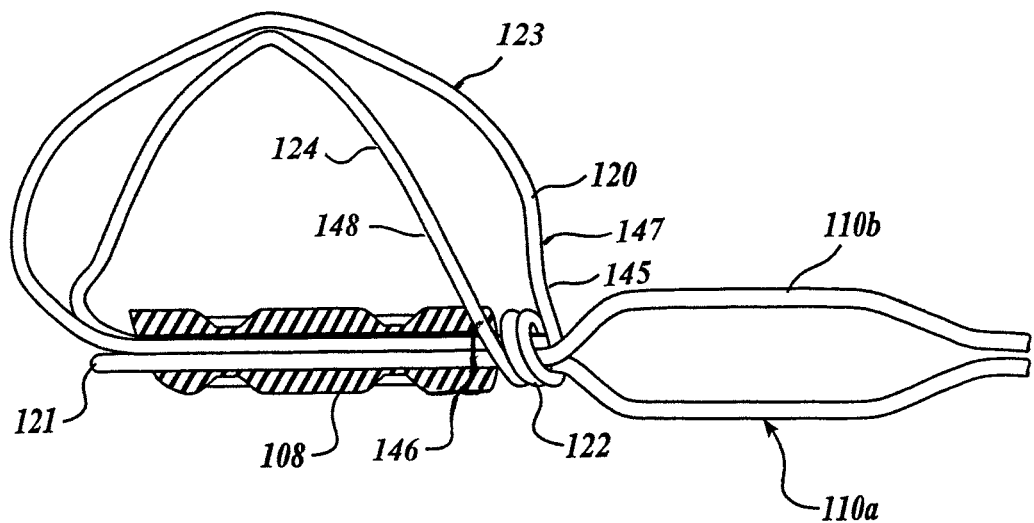
FIG. 4 illustrates a distal anchor of the embodiment shown in FIG. 3.

At the distal end of the support wire 102 is a distal anchor 120 that is formed of a flexible wire such as nitinol or some other shape memory material. As is best shown in FIGS. 3 and 4, the wire forming the distal anchor has one end positioned within the distal crimp tube 108. After exiting the distal end of the crimp tube 108, the wire forms a figure eight configuration whereby it bends upward and radially outward from the longitudinal axis of the crimp tube 108. The wire then bends back proximally and crosses the longitudinal axis of the crimp tube 108 to form one leg of the figure eight. The wire is then bent to form a double loop eyelet or loop 122 around the longitudinal axis of the support wire 102 before extending radially outwards and distally back over the longitudinal axis of the crimp tube 108 to form the other leg of the figure eight. Finally, the wire is bent proximally into the distal end of the crimp tube 108 to complete the distal anchor 120.

The distal anchor is expanded by sliding the double eyelet 122 of the distal anchor from a position that is proximal to the distal lock 110 on the support wire to a position that is distal to the distal lock 110. The bent-out portions 110a and 110b of distal lock 110 are spaced wider than the width of double eyelet 122 and provide camming surfaces for the locking action. Distal movement of eyelet 122 pushes these camming surfaces inward to permit eyelet 122 to pass distally of the lock 110, then return to their original spacing to keep eyelet 122 in the locked position.

The dimensions of the distal anchor are selected so that the diameter of the distal anchor in a plane perpendicular to the axis of the lumen in which the anchor is deployed is preferably between 100% and 300%, most preferably between 130% and 200%, of the diameter of the lumen prior to deployment. When treating mitral valve regurgitation by placement of the device in the coronary sinus, the diameter of the coronary sinus may expand over time after deployment. Oversizing the anchor combined with the inherent deformability and recoverability properties of the anchor material (particularly nitinol or some other shape memory material) enables the anchor to continue to expand from its initial deployment size as the lumen distends and expands over time.

Upon expansion, the distal anchor circumferentially engages the vessel wall with a radially outwardly directed force that is distributed unequally around the circumference of the anchor by distending the vessel wall in variable amounts along the axial length of the anchor. The unequal distribution of force helps the anchor contact the lumen wall securely by creating bumps and ridges that are not parallel to the central axis of the lumen. In its expanded configuration, the distal anchor's diameter is at least 150%-500% and most preferably 150%-300% of the anchor's diameter in the unexpanded configuration. The open cross-sectional area of the lumen through the anchor is at least 50%, and most preferably 80%-100% of the lumen cross-sectional area prior to redeployment of the anchor.

In addition, the metal coverage of the anchor, as defined by the percentage of the lumen surface area through which the device extends that is exposed to a metal surface, is between 5% and 30% and most preferably 10%. The wire used to form the distal anchor 120 is preferably nitinol having a diameter of between 0.0110" and 0.0150" and most preferably 0.0140 inches. Other shape memory materials may be used as well.

During insertion, a physician can tactilely feel when the eyelet 122 has been slid over the distal lock 110 in order to determine when the distal anchor has been set within a vessel lumen. In addition, if the anchor is misplaced, it can be collapsed by pulling the eyelet 122 proximally over the distal lock 110 and repositioning the anchor in the unexpanded configuration. The force required to capture the distal anchor is preferably less than 20 lbs. and more preferably less than 10 lbs.

FIG. 4 also illustrates how the crimp tube 108 is held in place between the distal lock 110 on the proximal side and the stop loop 121 at the distal end of the support wire 102. The wires of the distal anchor 120 exit the distal end of the crimp tube 108 at an angle of approximately 45 degrees before looping back over the length of the distal crimp tube 108. Therefore, the distal end of the anchor is relatively atraumatic to avoid damage to a vessel during placement.

Figure 5:
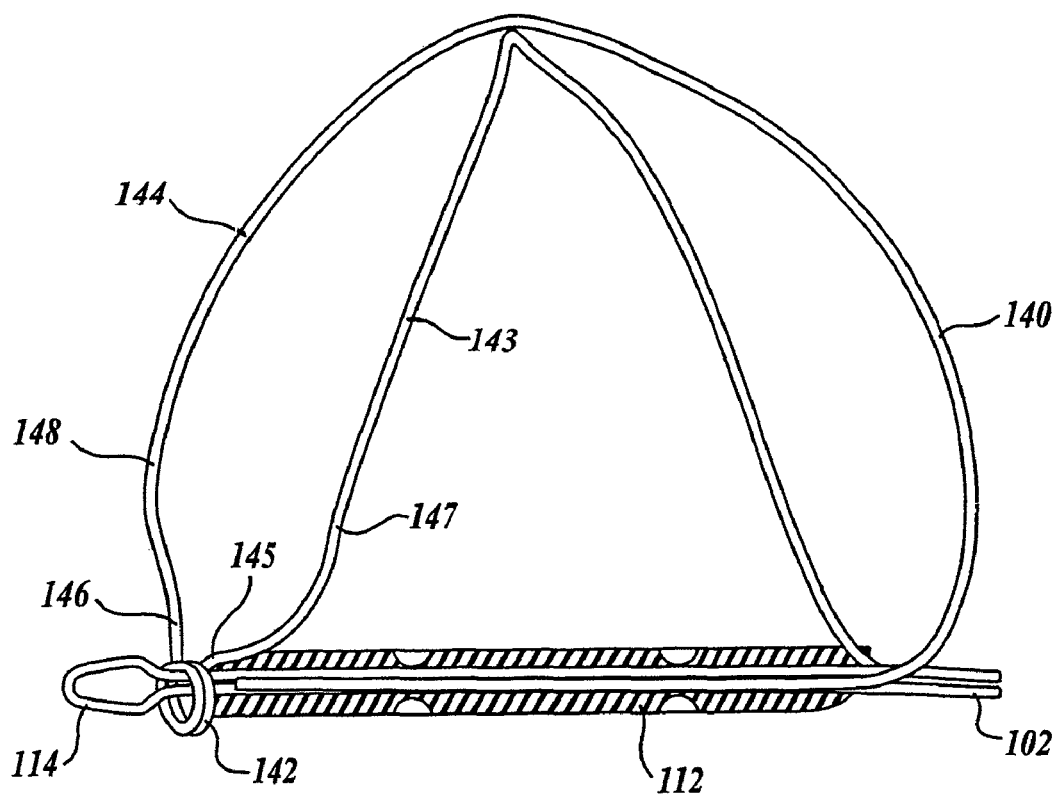
FIG. 5 illustrates a proximal anchor of the embodiment shown in FIG. 3.

At the proximal end of the intravascular support is a proximal anchor 140 that is preferably formed of a biocompatible, elastic wire such as stainless steel or a shape memory material such as nitinol. As is best shown in FIGS. 3 and 5, the proximal anchor 140 in one embodiment is made of a single length of wire having a first end positioned within a proximal crimp tube 112. The wire extends distally from the crimp tube 112 and bends radially outward and away from the longitudinal axis of the crimp tube 112 before being bent proximally and crossing the longitudinal axis of the crimp tube 112 in order to form a first leg of a figure eight configuration. The wire then is bent to form a double eyelet or loop 142 around the longitudinal axis of the support wire 102 wherein the eyelet 142 has a diameter that allows it to be forced over the proximal lock 114. After forming the eyelet 142, the wire extends outwardly and away from the longitudinal axis of the crimp tube 112 before being bent distally over and across the longitudinal axis of the crimp tube 112 to form the second leg of a figure eight. Finally, the wire is bent proximally and extends into the distal end of the crimp tube 112.

Figure 7:
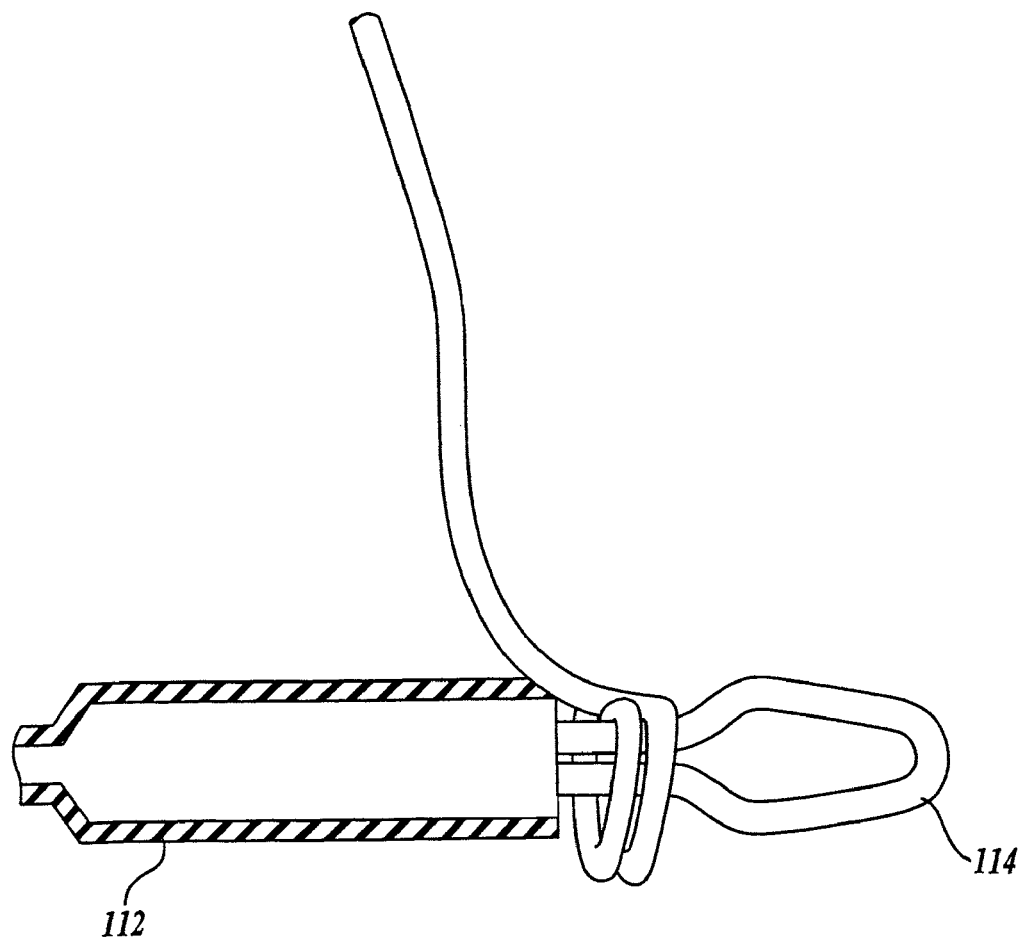
FIG. 7 illustrates a proximal lock at the proximal end of the intravascular support as shown in FIG. 3.

Like the distal anchor, the proximal anchor is expanded and locked by sliding the double eyelet 142 of the proximal anchor from a position that is proximal to the proximal lock 114 on the support wire to a position that is distal to the proximal lock 114. As can be seen in FIG. 7, the proximal lock 114 has an "arrowhead" shape whereby the proximal end of the lock is bent away from the longitudinal axis of the support wire at an angle that is less steep than the distal end of the proximal lock. The less steep section makes it easier to advance the eyelet 142 over the lock in the distal direction than to retrieve the eyelet 142 over the proximal lock 114 in the proximal direction. Distal movement of eyelet 142 cams the less steep proximal surfaces inward to permit eyelet 142 to pass distally of the lock 114, then return to their original spacing to keep eyelet 142 in the locked position.

As can be seen by comparing the proximal anchor 140 with the distal anchor 120 in FIG. 3, the proximal anchor has a larger radius of curvature because it is designed to fit within a larger diameter portion of the coronary sinus. The dimensions of the proximal anchor are selected so that the diameter of the proximal anchor in a plane perpendicular to the axis of the lumen in which the anchor is deployed is preferably between 100% and 300%, most preferably between 130% and 200%, of the diameter of the lumen prior to deployment. As with the distal anchor, oversizing the proximal anchor combined with the inherent deformability and recoverability properties of the anchor material (particularly nitinol or some other shape memory material) enables the anchor to continue to expand from its initial deployment size as the lumen distends and expands over time.

Upon expansion, the proximal anchor circumferentially engages the vessel wall with a radially outwardly directed a force that is distributed unequally around the circumference of the anchor by distending the vessel wall in variable amounts along the axial length of the anchor. As with the distal anchor, the unequal distribution of force helps the proximal anchor contact the lumen wall securely by creating bumps and ridges that are not parallel to the central axis of the lumen. In its expanded configuration, the proximal anchor's diameter is at least 200%-500% and most preferably 200%-300% of the anchor's diameter in the unexpanded configuration. The open cross-sectional area of the lumen through the anchor is at least 50% and most preferably 80%-100% of the lumen cross sectional area prior to redeployment of the anchor.

FIG. 3 illustrates an embodiment external to a patient's body. That is, the anchors are shown in expanded configurations and in the absence of bodily forces acting on the anchors.

In one embodiment of the invention, the proximal and distal anchors are oriented such that the planes of the anchors are offset with respect to each other by an angle of approximately 30 degrees. The offset helps the intravascular support 100 seat itself in the coronary sinus and vessel surrounding the mitral valve in certain mammals. However, it will be appreciated that if the support is designed for other uses, the proximal and distal anchors may be offset by more or less depending upon the anatomy of the intended destination.

Figure 6A:
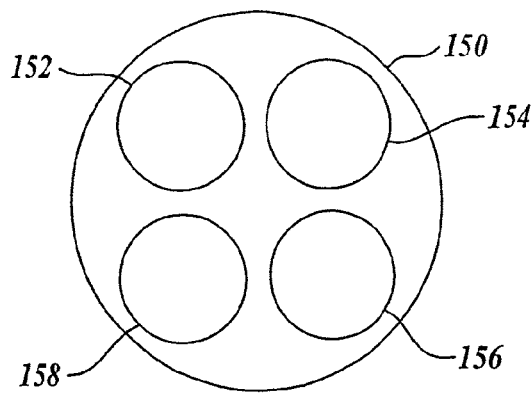
FIGS. 6A-6C are cross-sectional views of crimp tubes for use with one embodiment of the present invention.
Figure 6B:
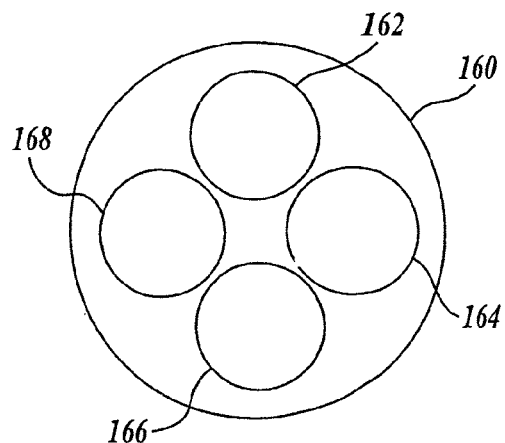
Figure 6C:
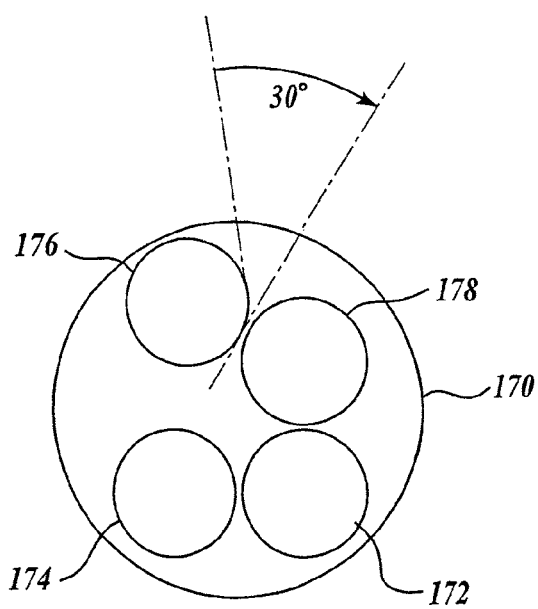

FIGS. 6A-6C illustrate cross-sectional views of the crimp tubes in which the wires that form the support wire 102 and proximal and distal anchors 120, 140 are threaded. In one embodiment, the crimp tubes comprise a biocompatible material such as titanium having a number of holes extending longitudinally through the tube through which the wires are threaded. In FIG. 6A, a tube 150 has four holes 152, 154, 156, 158 positioned in approximately a square configuration within the circumference of the tube 150. As shown in FIG. 6B, a tube 160 includes four holes 162, 164, 166, 168 therein that are positioned in a diamond configuration. FIG. 6C shows another tube 170 having four holes 172, 174, 176, 178. Here the holes 172, 174 lie in a first plane and the second pair of holes 176, 178 lie in a second plane that is offset from the plane of the holes 172, 174. By changing the orientation of the holes 176, 178 with respect to the holes 172, 174, the relative plane of wires passing through the holes can be adjusted. Thus in the example shown in FIG. 3, the proximal anchor may be formed with a crimp tube such as that shown in FIG. 6A or FIG. 6B while the proximal anchor may be formed in a crimp tube such as that shown in FIG. 6C in order to adjust the angular orientation between the proximal anchor and the distal anchor. In an alternative embodiment, the crimp tubes at the proximal and distal ends of the support wire 102 are the same and the angular offset between the proximal and distal anchor is achieved by bending the wires at the desired angle. Although the crimp tubes shown use one hole for each wire passing through the crimp tube, it will be appreciated that other configurations may be provided such as slots or other passages for the wires to pass through.

In another embodiment, the distal and proximal anchors are attached to the support wire by a wire, such as nitinol wire or other shape memory material. The attaching wire may be spiral wrapped around the base of each anchor and around the support wire. In another embodiment, each anchor may be attached to the support wire by wrapping the anchor wire around the support wire. In yet another embodiment, the two anchors and the support wire may be made from a single wire, such as nitinol wire or other shape memory material.

Figure 8:
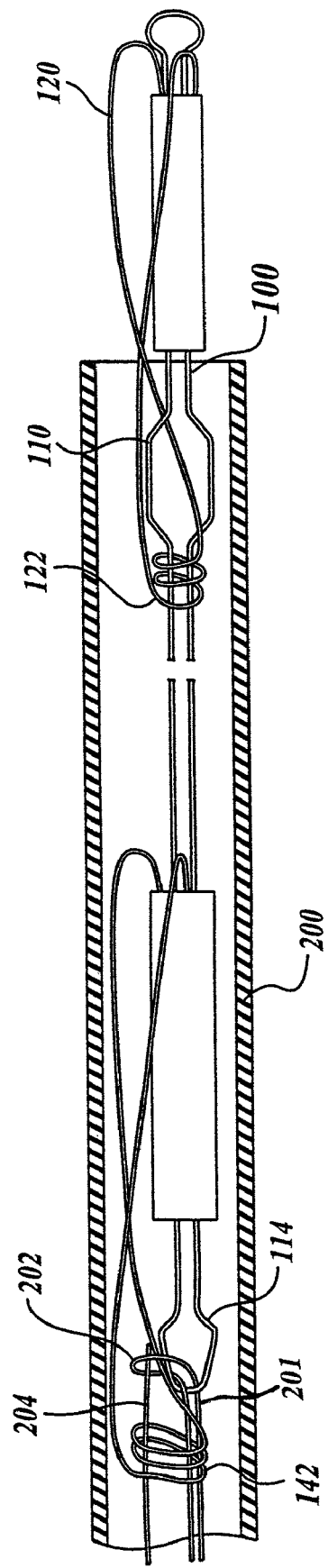
FIG. 8 illustrates how the embodiment of the intravascular support shown in FIG. 3 is deployed from a catheter.

FIG. 8 illustrates one method for delivering an intravascular support 100 in accordance with the present invention to a desired location in the body. As indicated above, intravascular support 100 is preferably loaded into and routed to a desired location within a catheter 200 with the proximal and distal anchors in a collapsed or deformed condition. That is, the eyelet 122 of the distal anchor 120 is positioned proximally of the distal lock 110 and the eyelet 142 of the proximal anchor 140 is positioned proximal to the proximal lock 114. The physician ejects the distal end of the intravascular support from the catheter 200 into the lumen by advancing the intravascular support or retracting the catheter or a combination thereof. A pusher (not shown) provides distal movement of the intravascular support with respect to catheter 200, and a tether 201 provides proximal movement of the intravascular support with respect to catheter 200. Because of the inherent recoverability of the material from which it is formed, the distal anchor begins to expand as soon as it is outside the catheter. Once the intravascular support is properly positioned, the eyelet 122 of the distal anchor is pushed distally over the distal lock 110 so that the distal anchor 120 further expands and locks in place to securely engage the lumen wall and remains in the expanded condition. Next, the proximal end of the support wire 102 is tensioned by applying a proximally-directed force on the support wire and distal anchor to apply sufficient pressure on the tissue adjacent the support wire to modify the shape of that tissue. In the case of the mitral valve, fluoroscopy, ultrasound or other imaging technology may be used to see when the support wire supplies sufficient pressure on the mitral valve to aid in its complete closure with each ventricular contraction without otherwise adversely affecting the patient. A preferred method of assessing efficacy and safety during a mitral valve procedure is disclosed in copending U.S. patent application Ser. No. 10/366,585, filed Feb. 12, 2003, and titled "Method of Implanting a Mitral Valve Therapy Device," the disclosure of which is incorporated herein by reference. Once the proper pressure of the support wire has been determined, the proximal anchor is deployed from the catheter and allowed to begin its expansion. The eyelet 142 of the proximal anchor 140 is advanced distally over the proximal lock 114 to expand and lock the proximal anchor, thereby securely engaging the lumen wall and maintaining the pressure of the support wire against the lumen wall. Finally, the mechanism for securing the proximal end of the intravascular support can be released. In one embodiment, the securement is made with a braided loop 202 at the end of tether 201 and a hitch pin 204. The hitch pin 204 is withdrawn thereby releasing the loop 202 so it can be pulled through the proximal lock 114 at the proximal end of the intravascular support 100.

In many contexts, it is important for the device to occupy as little of the lumen as possible. For example, when using the device and method of this invention to treat mitral valve regurgitation, the device should be as open as possible to blood flow in the coronary sinus (and to the introduction of other medical devices, such as pacing leads) while still providing the support necessary to reshape the mitral valve annulus through the coronary sinus wall. The combination of the device's open design and the use of nitinol or some other shape memory material enables the invention to meet these goals. When deployed in the coronary sinus or other lumen, the device preferably occupies between about 1.5% and about 5.5% of the overall volume of the section of lumen in which it is deployed.

In many embodiments of the invention, the use of a shape memory material such as nitinol is particularly important. The percentage of shape memory material by volume in the device is preferably between about 30% and 100%, most preferably between about 40% and 60%.

In some instances, it may be necessary to move or remove an intravascular support after deployment by recapturing the device into a catheter. Prior to deployment of the proximal anchor, the distal anchor may be recaptured into the delivery catheter by simultaneously holding the device in place with tether 201 while advancing catheter distally over distal anchor 120 so that the entire device is once again inside catheter 200. The distally directed force of the catheter collapses distal anchor 120 into a size small enough to fit into catheter 200 again. Likewise, after deployment of both anchors but prior to releasing the securement mechanism as described above, the intravascular support may be recaptured into the delivery catheter by simultaneously holding the device in place with tether 201 while advancing catheter distally first over proximal anchor 140, over support wire 102, and finally over distal anchor 120. The distally directed forced of catheter 200 collapses anchors 120 and 140 into a size small enough to fit into catheter 200 again. If the securement mechanism has been detached from the device prior to recapture, the device still may be recaptured into the delivery catheter or another catheter by grasping the proximal end of the device with a grasper or tether and by advancing the catheter distally over the device.

In one embodiment of the invention, proximal anchor 140 includes a recapture guidance and compression element. In the embodiment shown in FIG. 5, the slope of the two proximal arms 143 and 144 of proximal anchor 140 is small in proximal portions 145 and 146 of the arms, then increases in more distal portions 147 and 148 of the arms. This shape guides the catheter to move distally over the anchor more easily and to help compress the anchor to a collapsed shape as the catheter advances during recapture.

Likewise, the two proximal arms 123 and 124 of distal anchor 120 have a shallower slope in their proximal portions 145 and 146 and an increased slope in more distal portions 147 and 148. While recapture of the distal anchor is somewhat easier due to its smaller size compared to the proximal anchor, this recapture guidance and compression feature enhances the ease with which recapture is performed.

Figure 9:
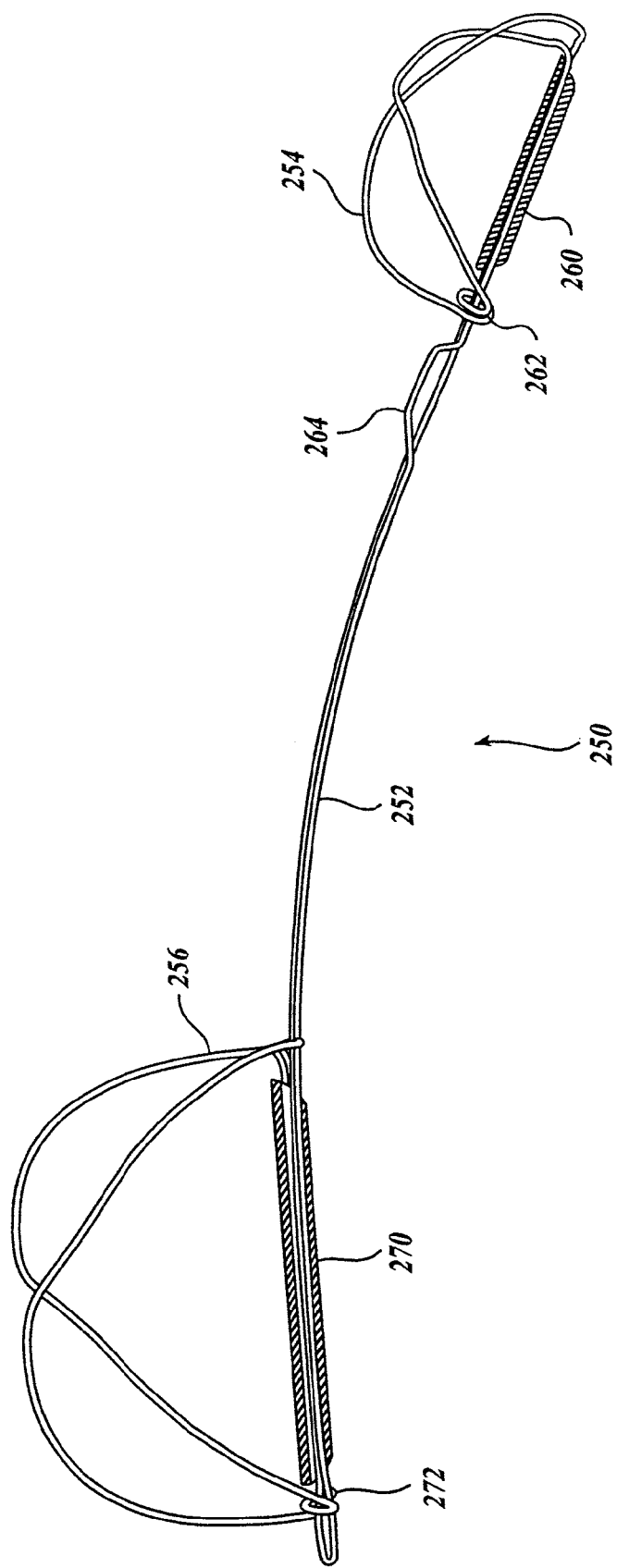
FIG. 9 illustrates an intravascular support in accordance with another embodiment of the present invention.
Figure 10:
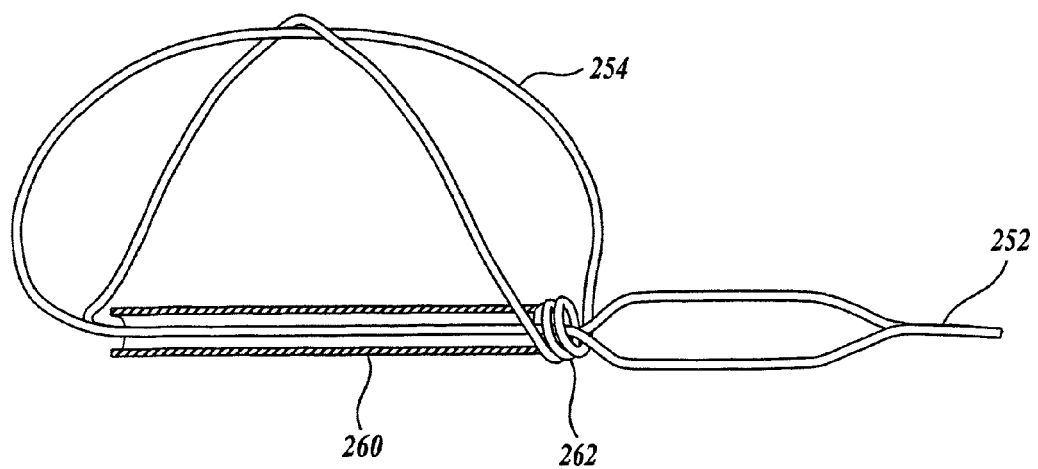
FIG. 10 illustrates a distal anchor of the intravascular support shown in FIG. 9.

FIG. 9 illustrates an alternative embodiment of the intravascular support of the present invention. In this embodiment, an intravascular support 250 has a support wire 252 and a distal anchor 254 and a proximal anchor 256. In the embodiment shown in FIG. 9, the distal anchor 254 is made from the same wire used to form the support wire 252. As best shown in FIG. 10, the wire used to form the support wire 252 extends distally through a distal crimp tube 260 before looping radially outward and returning proximally and across the longitudinal axis of the crimp tube 260 to form one leg of a figure eight. The wire then winds around the axis of the suspension wire 252 to form an eyelet 262. The wire then continues radially outward and distally across the longitudinal axis of the crimp tube 260 to form the second leg of a figure eight. After forming the figure eight, the wire enters the distal end of the crimp tube 260 in the proximal direction to form the other half of the support wire 252. A distal lock 264 is formed proximal to the distal crimp tube 260 by outwardly extending bends in the wires that form the support wire 252. The distal lock 264 prevents the double eyelet 262 from sliding proximally and collapsing the distal anchor 254 when positioned in a vessel.

Figure 11:
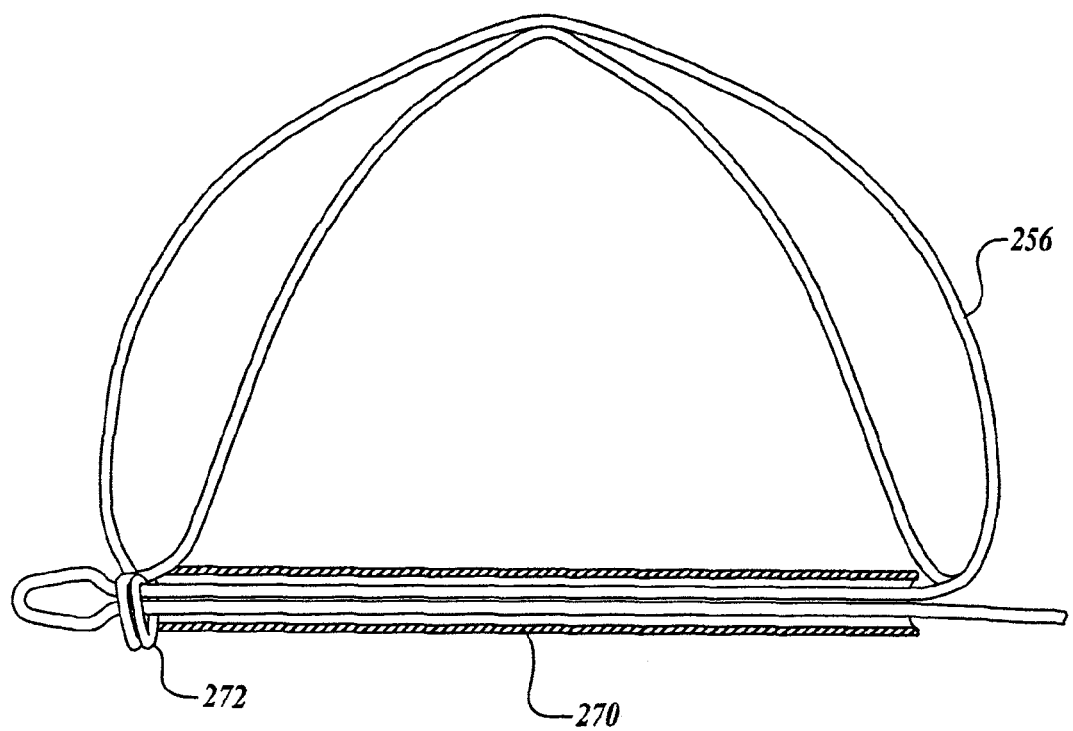
FIG. 11 illustrates a proximal anchor of the intravascular support shown in FIG. 9.

As shown in FIG. 11, a proximal anchor 256 is constructed in a fashion similar to the proximal anchor 140 shown in FIG. 3. That is, the proximal anchor 256 is formed of a separate wire than the wire used to form the support wire 252 and distal anchor 254. The wire of the proximal anchor has one end within a proximal crimp tube 270. The wire extends distally out of the end of the crimp tube and bends radially outward before returning back and across the longitudinal axis of the crimp tube 270. At the proximal end of the crimp tube 270, the wire of the proximal anchor forms a double eyelet 272 around the longitudinal axis of the support wire 252. The wire then continues radially outward and distally over the longitudinal axis of the crimp tube 270 to form the second leg of the figure eight whereupon it is bent proximally into the distal end of the crimp tube 270.

Figure 12:
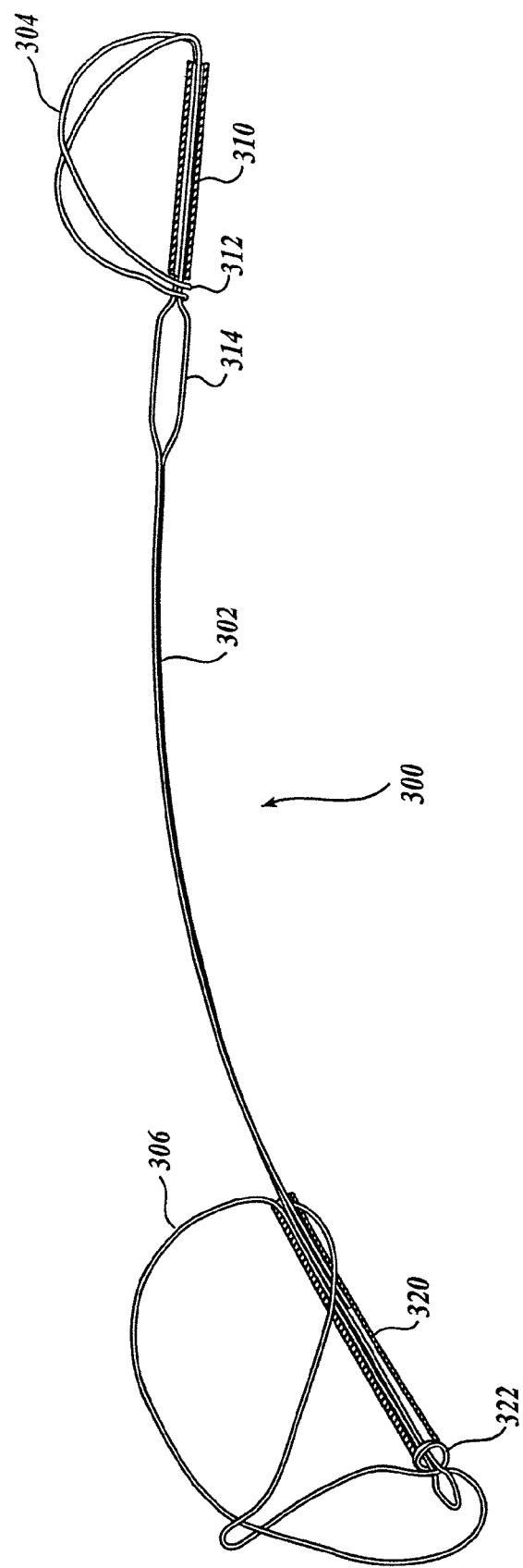
FIG. 12 illustrates yet another embodiment of an intravascular support in accordance with the present invention.
Figure 13:
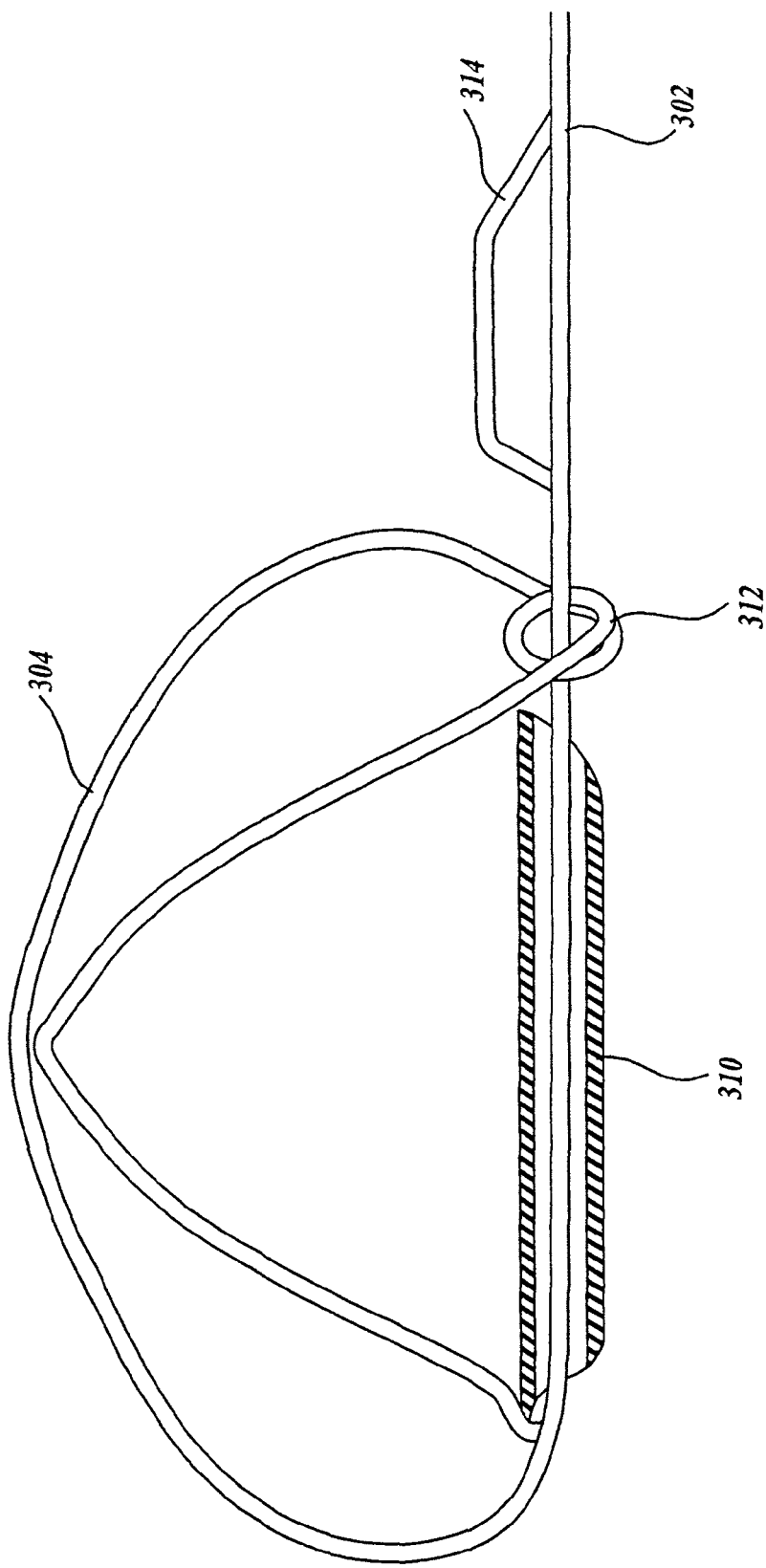
FIG. 13 illustrates a distal anchor of the intravascular support shown in FIG. 12.

FIG. 12 shows yet another embodiment of an intravascular support in accordance with the present invention. Here, an intravascular support 300 comprises a support wire 302, a distal anchor 304 and a proximal anchor 306. As in the embodiment shown in FIG. 9, the distal anchor 304 and the support wire 302 are formed of the same wire. To form the distal anchor, the wire extends distally through a distal crimp tube 310 and exits out the distal end before extending radially outward and bending back and across the longitudinal axis of the crimp tube 310 to form one leg of a figure eight. The loop then forms an eyelet 312 around the longitudinal axis of the support wire 302 before bending radially outward and distally across the longitudinal axis of the crimp tube 310 to form a second leg of the figure eight. The wire then enters the distal end of the crimp tube 310 in the proximal direction. The support wire 302 may have one or two outwardly extending sections that form a distal stop 314 to maintain the position of the eyelet 312 once the distal anchor is set in the expanded configuration.

Figure 14:
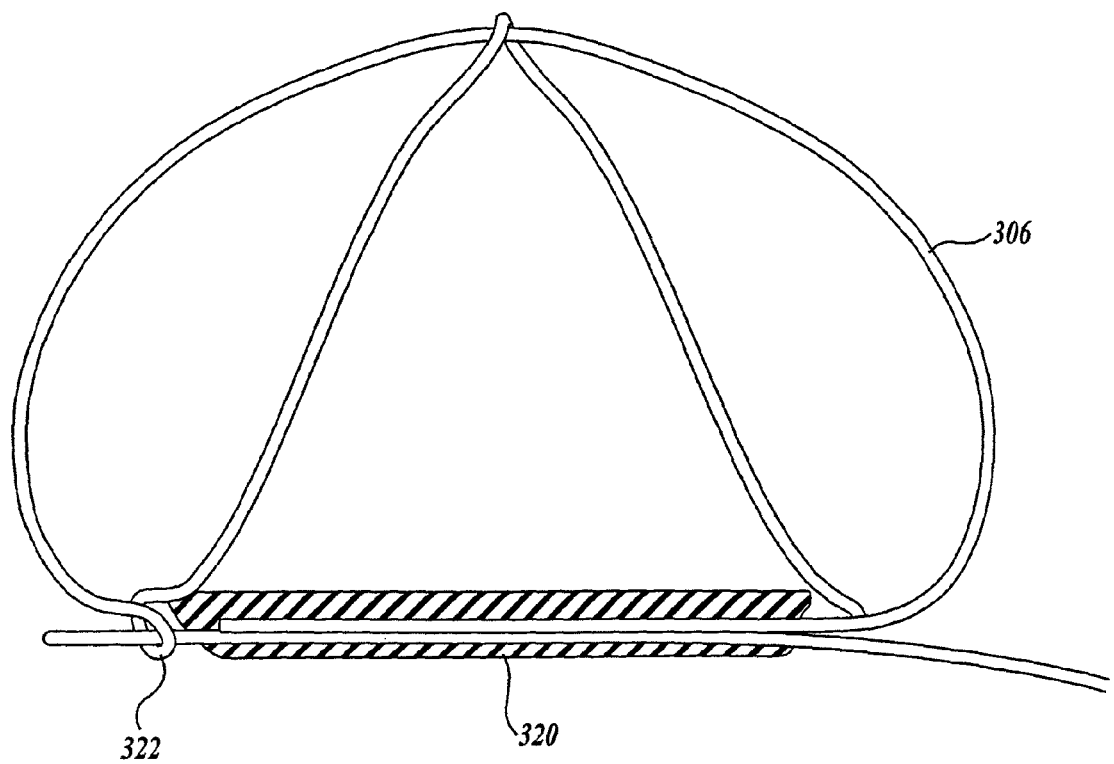
FIG. 14 illustrates a proximal anchor of the intravascular support shown in FIG. 12.
Figure 15:
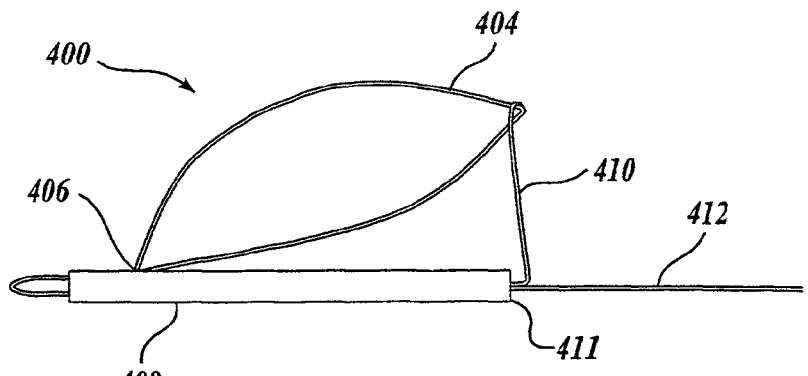
FIG. 15 illustrates an anchor and strut according to another embodiment of the invention.

The proximal anchor 306 is formed from a separate wire as shown in FIG. 14. The wire has one end positioned within the proximal crimp tube 320 that extends distally outward and radially away from the longitudinal axis of the crimp tube 320 before being bent proximally and across the longitudinal axis of the crimp tube 320 to form one leg of the figure eight. The wire then winds around the longitudinal axis of the support wire to form an eyelet 322 before being bent distally and across the longitudinal axis of the crimp tube 320 to enter the distal end of the crimp tube 320 in the proximal direction. As will be appreciated, the proximal crimp tube 320 of the embodiment shown in FIG. 12 holds four wires wherein the distal crimp tube 310 need only hold two wires.

FIGS. 15-18 show other embodiments of the invention. In the embodiment shown in FIG. 15, the intravascular support has an anchor 400 formed as a loop 404 emerging from a window 406 in a crimp tube 408. Extending from one end 411 of crimp tube 408 is a support strut 410 which connects with loop 404. Also extending from the crimp tube 408 is a support wire 412. Loop 404 and support 410 may be formed from nitinol, stainless steel, or any other appropriate material. The intravascular support includes another anchor. The intravascular support of this embodiment may be delivered and deployed in the manner discussed above with respect to the embodiment described above.

Figure 16:
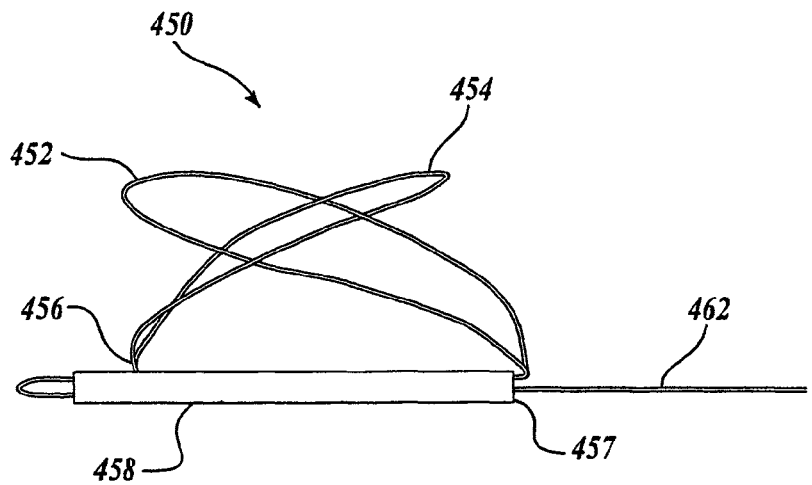
FIG. 16 illustrates a double loop anchor according to another embodiment of the invention.

FIG. 16 shows another embodiment of an anchor 450 for an intravascular support. Anchor 450 is formed from two loops 452 and 454 emerging from a window 456 and an end 457 of a crimp tube 458. A support wire 462 also extends from the crimp tube. Loops 452 and 454 may be formed from nitinol, stainless steel, or any other appropriate material. The intravascular support includes another anchor. The intravascular support of this embodiment may be delivered and deployed in the manner discussed above with respect to the embodiment described above.

Figure 17:
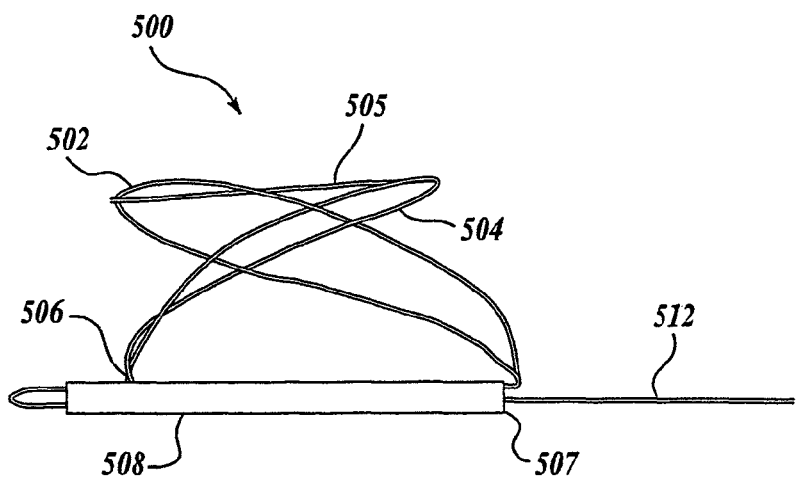
FIG. 17 illustrates a double loop anchor with a cross strut according to another embodiment of the invention.

FIG. 17 shows yet another embodiment of an anchor 500 for an intravascular support according to this invention. Anchor 500 is formed from two loops 502 and 504 emerging from a window 506 and an end 507 of a crimp tube 508. A cross strut 505 connects the loops. A support wire 512 also extends from the crimp tube. Loops 502 and 504 and strut 505 may be formed from nitinol, stainless steel, or any other appropriate material. The intravascular support includes another anchor. The intravascular support of this embodiment may be delivered and deployed in the manner discussed above with respect to the embodiment described above.

Figure 18:
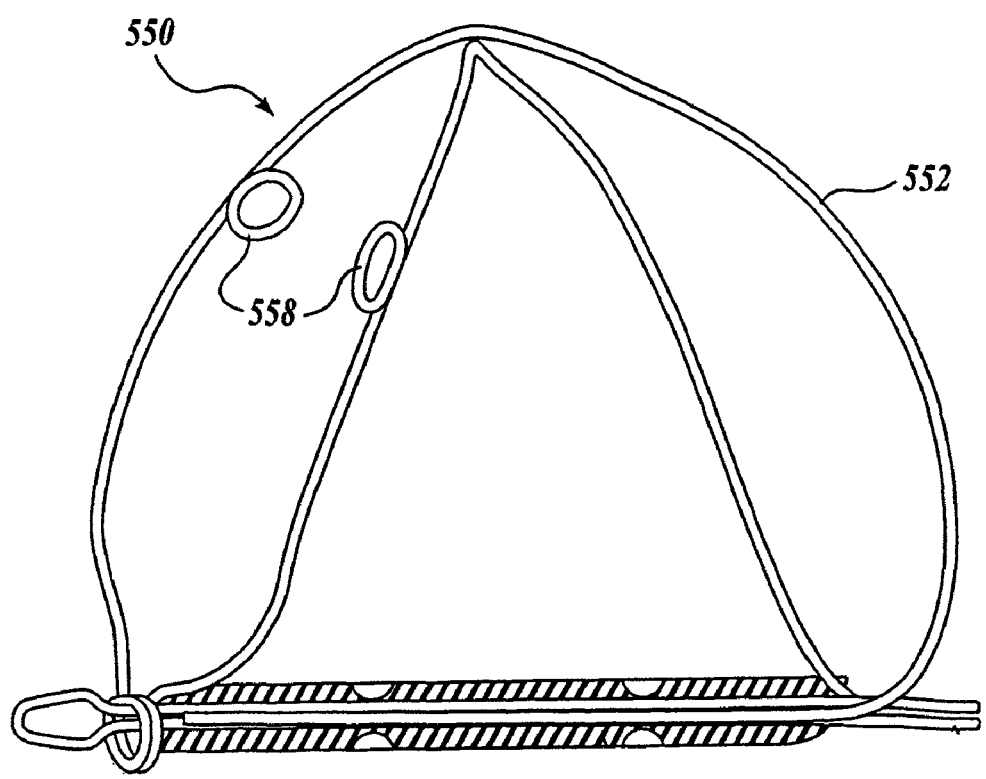
FIG. 18 illustrates an anchor with torsional springs according to another embodiment of the invention.

FIG. 18 is a modification of the embodiment shown in FIGS. 3-7. In this embodiment, torsional springs 558 of proximal anchor 550 have been formed as single loops or eyelets in the anchor's wire 552. These springs make the anchor 550 more compliant by absorbing some of the force applied to the anchor during locking. While FIG. 18 shows a proximal anchor with two springs 558, any number of springs could be used on either the proximal or the distal anchor.

While the preferred embodiment of the invention has been illustrated and described, it will be appreciated that various changes can be made therein without departing from the spirit and scope of the invention.

What is claimed is:

1. A device for treating mitral valve regurgitation, comprising:
   a distal anchor having a collapsed configuration within a delivery device and an expanded configuration with an expanded diameter;
   a proximal anchor having a collapsed configuration within the delivery device and an expanded configuration with an expanded diameter; and
   a connecting element connecting the distal and proximal anchors, wherein the diameter of the proximal anchor in the expanded configuration is at least about 133% greater than the diameter of the distal anchor in the expanded configuration, wherein each of the distal and proximal anchors are adapted to have the expanded configurations with the expanded diameters external to a patient's body.

2. The device of claim 1 wherein the distal and proximal anchors each have collapsed diameters in their collapsed configurations, and wherein the collapsed diameter of the distal anchor within the delivery device is substantially the same as the collapsed diameter of the proximal anchor within the delivery device.

3. The device of claim 1 wherein the diameter of the proximal anchor in the expanded configuration is at least about 200% greater than the diameter of the distal anchor in the expanded configuration.

4. The device of claim 1 wherein the diameter of the proximal anchor in the expanded configuration is at least about 333% greater than the diameter of the distal anchor in the expanded configuration.

5. The device of claim 1 further comprising a distal lock adapted to lock the distal anchor in a locked configuration.

6. The device of claim 5 wherein the distal lock is adapted to lock the distal anchor in the expanded configuration.

7. The device of claim 1 further comprising a proximal lock adapted to lock the proximal anchor in a locked configuration.

8. The device of claim 7 wherein the proximal lock is adapted to lock the proximal anchor in the expanded configuration.

* * * * *